(12) United States Patent
Weisbeck et al.

(10) Patent No.: US 6,504,039 B2
(45) Date of Patent: Jan. 7, 2003

(54) SUPPORTED CATALYST AND THE PROCESS FOR PREPARING THE SAME

(75) Inventors: Markus Weisbeck, Köln-Holweide (DE); Ernst-Ulrich Dorf, Krefeld (DE); Gerhard Wegener, Mettmann (DE); Christoph Schild, Leverkusen (DE); Bernhard Lücke, Berlin (DE); Herbert Dilcher, Rangsdorf (DE); Ulrich Schülke, Berlin (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/146,248

(22) Filed: May 15, 2002

(65) Prior Publication Data

US 2002/0165404 A1 Nov. 7, 2002

Related U.S. Application Data

(62) Division of application No. 09/601,260, filed on Sep. 18, 2000.

(51) Int. Cl.$^7$ .......................... C07D 301/10; B01J 37/03
(52) U.S. Cl. ........................ 549/523; 502/103; 502/107
(58) Field of Search ................ 502/103, 107; 549/523

(56) References Cited

U.S. PATENT DOCUMENTS

| | | | |
|---|---|---|---|
| 4,839,327 A | 6/1989 | Haruta et al. | 502/243 |
| 4,937,219 A | 6/1990 | Haruta et al. | 502/174 |
| 5,051,394 A | 9/1991 | Haruta et al. | 502/324 |
| 5,623,090 A | 4/1997 | Haruta et al. | 568/360 |
| 5,929,258 A | 7/1999 | Hayashi et al. | 549/523 |
| 5,932,750 A | 8/1999 | Hayashi et al. | 549/523 |
| 5,939,569 A | 8/1999 | Jones et al. | 549/512 |
| 5,965,754 A | 10/1999 | Clark et al. | 549/533 |
| 6,008,389 A | 12/1999 | Grosch et al. | 549/533 |
| 6,034,028 A | 3/2000 | Hayashi et al. | 502/243 |

FOREIGN PATENT DOCUMENTS

| | | |
|---|---|---|
| EP | 0 709 360 | 5/1996 |
| EP | 0 850 936 | 7/1998 |
| FR | 2771310 | 5/1999 |
| WO | 97/47386 | 12/1997 |
| WO | 98/00413 | 1/1998 |
| WO | 99/43431 | 2/1998 |

OTHER PUBLICATIONS $3^{rd}$ World Congress on Oxidation Catalysis, (month unavailable), 1977, pp. 965–970, Yuri A. Kalvachev et al, "Selective Partial Oxidation of Propylene to Propylene Oxide on Au/Ti–MCM Catalysts in the Presence of Hydrogen and Oxygen".
S. Tsubota et al.,: ACS Symp Ser., Bd. 552, 1994, pp. 420–428, XP002114494, & Chemical Abstracts, vol. 120, No. 16, Apr. 18, 1994, Abstract No. 201527, XP002114498.
M. Haruta et al.: Res. Chem. Intermed., Bd. 24, Nr. 3, 1998, pp. 329–336, XP002114495.
T. Hayashi et al.: J. Catal., Bd. 178, Nr. 2, 1998, pp. 566–575, XP002114496.
B.S. Uphade et al.: Chem. Lett., Bd. 12, 1998, pp. 1277–1278, XP002114497.

*Primary Examiner*—T. A. Solola
(74) *Attorney, Agent, or Firm*—Joseph C. Gil; Carolyn M. Sloane

(57) ABSTRACT

The present invention relates to supported catalysts which are composed of titanium oxide hydrates coated with nanoscale gold particles. The catalysts of the present invention have increased activity over known catalysts.

3 Claims, No Drawings

SUPPORTED CATALYST AND THE PROCESS FOR PREPARING THE SAME

CROSS-REFERENCE TO RELATED APPLICATIONS

This application is a divisional application of U.S. application Ser. No. 09/601,260, filed on Sep. 18, 2000 now pending.

The invention relates to a catalytic gas phase process for the preparation of epoxides from unsaturated hydrocarbons by oxidation with molecular oxygen in the presence of molecular hydrogen and catalysts for this process which are coated with nanoscale gold particles.

In general, direct oxidations of unsaturated hydrocarbons with molecular oxygen in the gas phase do not proceed below 200° C. —even in the presence of catalysts and it is therefore difficult to prepare oxidation-sensitive oxidation products, such as e.g. epoxides, alcohols or aldehydes, selectively, since the secondary reactions of these products often proceed faster than the oxidation of the olefins employed themselves.

Propene oxide is one of the most important base chemicals of the chemical industry. Its field of use lies in the plastics sector with a proportion of more than 60%, specifically for the preparation of polyether-polyols for the synthesis of polyurethanes. In addition, even greater proportions of the market are covered by propene oxide derivatives in the field of glycols, in particular in lubricants and anti-freezes.

About 50% of propene oxide worldwide is currently synthesized via the "chlorohydrin process". A further 50%, with an increasing trend, is supplied by the "oxirane process".

In the chlorohydrin process (F. Andreas et al.; Propylenchemie [Propylene chemistry], Berlin 1969), chlorohydrin is first formed by reaction of propene with HOCl (water and chlorine), and propene oxide is then formed from the chlorohydrin by splitting off HCl with a base. The process is cost-intensive, but with appropriate optimization has a high selectivity (>90%) with high conversions. The loss of chlorine in the chlorohydrin process in the form of worthless solutions of calcium chloride and sodium chloride and the associated high salt load in the waste water led early on to the search for chlorine-free oxidation systems.

The oxidation processes use organic compounds instead of the inorganic oxidizing agent HOCl to transfer oxygen to propene. This indirect epoxidation is based on the fact that in the liquid phase organic peroxides, like hydroperoxides, can transfer their peroxide oxygen selectively to olefins to form epoxides. During this process, the hydroperoxides are converted into alcohols and the peroxycarboxylic acids are converted into acids. Hydroperoxides are produced from the corresponding hydrocarbon by autoxidation with air or molecular oxygen. A serious disadvantage of indirect oxidation is the economic dependence of the propene oxide value on the market value of the coupled product and the cost-intensive preparation of the oxidizing agent.

With titanium silicalite (TS 1) as a catalyst (Notari et al., U.S. Pat. No. 4,410,501 and U.S. Pat. No. 4,701,428), it was possible for the first time to epoxidize propene with hydrogen peroxide in the liquid phase under very mild reaction conditions with selectivities of >90% (Clerici et al., EP-A 230 949).

Propene oxidation is also achieved with a low yield in the liquid phase on titanium silicalites containing platinum metal with a gas mixture comprising molecular oxygen and molecular hydrogen (JP-A 92/352771).

U.S. Pat. No. 5,623,090 (Haruta et al.) describes a gas phase direct oxidation of propene to propene oxide with a 100% selectivity for the first time. This is a catalytic gas phase oxidation with molecular oxygen in the presence of the reducing agent hydrogen. Commercially available titanium dioxide coated with nanoscale gold particles is used as the catalyst. Nanoscale gold particles here are understood as meaning particles having a diameter in the nm range. The propene conversion and the propene oxide yield are stated as a maximum of 2.3%. The $Au/TiO_2$ catalysts described achieve the approx. 2% propene conversion for only a very short time; e.g. the typical half-lives at moderate temperatures (40–50° C.) are still unsatisfactory (Haruta et al., 3rd World Congress on Oxidation Catalysis 1997, p. 965–970, FIG. 6). This process thus has the disadvantage that the yield of epoxide, which is in any case low, is severely reduced further by rapid deactivation.

For economic use, the development of catalysts with significantly better initial activities with a greatly increased catalyst life therefore continues to be absolutely necessary.

The invention therefore provides a process for the oxidation of unsaturated hydrocarbons in the gas phase in the presence of a hydrogen/oxygen mixture, if appropriate with the addition of an inert gas, on a supported catalyst coated with gold particles, characterized in that a calcined catalyst which has been prepared from optionally doped titanium oxide hydrate and is coated with nanoscale gold particles is employed.

The process according to the invention can be used on all olefins. Since the gas phase oxidation expediently takes place at low temperatures (<120° C.) on the basis of the higher selectivities which can be achieved, it is possible to oxidize all unsaturated hydrocarbons from which are formed those oxidation products of which the partial pressure is sufficiently low for the product to be removed constantly from the catalyst. Unsaturated hydrocarbons having up to twelve carbon atoms, in particular ethene, propene, 1-butene or 2-butene, are preferred.

The preparation of the catalyst has a decisive influence on the catalyst activity. The catalysts are preferably prepared here by the "deposition-precipitation" method. In this, an aqueous solution of an inorganic or organic gold compound is added dropwise to a stirred aqueous suspension of the titanium oxide hydrate used as the catalyst support. A water-containing solvent is preferably used. Other solvents, such as e.g. alcohols, can also be employed. When bases (e.g. sodium carbonate or alkali metal or alkaline earth metal hydroxide solution) are added to this gold(III) salt solution up to a pH of 7–8.5, gold precipitates out on the titanium oxide hydrate surface in the form of Au(III) chlorohydroxo or oxohydroxo complexes or as gold hydroxide. To bring about a uniform deposition of ultrafine gold particles, the change in the pH must be controlled by slow dropwise addition of this alkaline aqueous solution. Since in an excess of alkali metal hydroxide solution the gold compounds deposited dissolve again to form aurates ($[Au(OH)_4]^-$ or $AuO_2^-$), for this reason a pH of between 7–8.5 must be established.

Precipitated gold(III) hydroxide cannot be isolated as such, but is converted into the metahydroxide AuO(OH) or $Au_2O_3$ on drying, which decomposes to elemental gold with the release of oxygen when calcined above 150° C. The nanoscale gold particles generated in this way are immobilized firmly adhering to the support surface, and have particle diameters of <10, preferably <6 nm. The amount of gold applied to the support depends on various variables, thus e.g. on the surface area, on the pore structure and on the chemical nature of the surface of the support. The properties of the support thus play an important role for the catalytic action.

Surprisingly, it has been found that when amorphous hydrated titanium oxide hydrates of high surface area are employed for coating with gold, the catalytic activities in the epoxidation of propene to propene oxide are drastically higher. These titanium oxide hydrates employed have water contents of 5 to 50 wt. % and surface areas of >50 m$^2$/g. Initial propene oxide yields of >4% e.g. are obtained with a catalyst which has been prepared on the basis of titanium oxide hydrate and comprises 0.5 wt. % gold.

The water content of the titanium oxide hydrates employed is usually between 5 and 50 wt. %, preferably between 7–20 wt. %. In the preparation of the catalyst, gold is applied to the titanium oxide hydrate in a precipitation step in the form of Au(III) compounds. However, the support loaded in this manner still has no catalytic activity. Only calcining in a stream of air at 350 to 500° C. makes a catalytically active material out of this precursor.

Low sulfate contents in the $TiO(OH)_n$ precursors surprisingly have the effect of a drastic improvement in the catalytic properties of the catalysts prepared with them. Catalysts based on titanium oxide hydrate with a sulfate content of between 0.1 and 6 wt. %, preferably 0.2–1 wt. %, are therefore preferably employed. The sulfate can be added during the titanium oxide hydrate preparation, or subsequently by treatment of the titanium oxide hydrates with reagents (e.g. sulfuric acid or sodium sulfate).

The concentration of the soluble gold compound in the stirred suspension has a significant influence on the catalytic activity of the catalyst prepared therefrom. By repeating the precipitation operation several times with small amounts of gold (e.g. with 0.5 wt. % gold each time), catalysts with significantly increased catalytic activities compared with catalysts with the same high gold loading which has been applied in one step can be prepared. Catalysts on which amounts of gold of between 0.05 to 10 wt. %, preferably 0.1 to 1 wt. %, have been applied repeatedly to the support by the "deposition-precipitation" process described, after washing and drying, are therefore preferably employed in the process according to the invention. When used in the direct oxidation of propene with molecular oxygen in the presence of molecular hydrogen, the catalyst prepared in this way according to the invention gives propene oxide with yields of >4% at selectivities of >97%.

In the preparation of the catalyst, the reduction of the gold hydroxides precipitated on the surface takes place during the calcining. If selected reducing agents (e.g. sodium citrate, magnesium citrate, . . .) are added during the preparation of the catalyst, the catalytic activities can be increased slightly.

The specific synergistic interaction between the nanoscale gold and the $TiO(OH)_n$ support is also achieved if the two components are applied to additional other supports (e.g. $SiO_2$, $Al_2O_3$, ZnO).

The amounts of catalyst employed and the amounts of gas employed are not limited. The "space velocity" of the gas stream through the catalyst bed should usually be approx. 0.5 to 20 l/g cat×h$^{-1}$.

The process according to the invention is carried out in the presence of the gases oxygen and hydrogen, if appropriate with the addition of inert gas. In the presence of these gases, the oxygenates propene oxide and acetone are also found at 150° C., in addition to the main products water, propane and $CO_2$. At a temperature between 30–60° C., only water and traces of other components (approx. 1%, based on PO) are found in addition to the main product propylene oxide (approx. 4% yield).

The composition of the gas phase, comprising propene, oxygen, hydrogen and possibly an inert gas, is important not only for the space/time yield, but also for safety. All molar compositions of the gases propene/oxygen/hydrogen/nitrogen can be employed in theory. Gas mixtures of oxygen and hydrogen are known to be explosive in certain compositions (explosive gas). Surprisingly, it has been found that the oxidation reaction described above can be carried out under approximately "hydrogenating conditions" outside the explosion limits. "Hydrogenating conditions" means that, in addition to an excess of hydrogen, only very small amounts of oxygen are employed. The following gas ratios are therefore employed for the oxidation reaction: $H_2$/hydrocarbon/oxygen/nitrogen: 20–80 vol. %/10–50 vol. % /1–10 vol. %/0–50 vol. %. Preferably, $H_2$/hydrocarbon/oxygen/nitrogen: 30–75%/15–40%/3–8%/0–10%. The molecular oxygen employed for the reaction can have various origins, e.g. pure oxygen, air or other oxygenlinert gas mixtures.

In addition to the process according to the invention for the oxidation of unsaturated hydrocarbons, the invention furthermore also provides the catalyst employed in this process.

EXAMPLES

Direct Oxidation of Propene to Propene Oxide

Standard reaction conditions: The reactor is a fixed bed tube reactor (1 cm diameter, 20 cm length) of double-walled glass, which is temperature-controlled at 46° C. by means of a water thermostat. The reactor is preceded by a static mixing and temperature-controlling zone. The gold supported catalyst is initially introduced on to a glass frit. The catalyst loading is 1.8 l/g cat. h. The educt gases are metered into the reactor from the top downwards by means of flow regulators. The educt gas ratios are $O_2/H_2/C_3H_6$: 0.1/1.3/0.4 l/h. The reaction gas mixture is analysed by means of gas chromatography with an FID (all oxygen-containing organic compounds, exception $CO_2$) and TCD detector (permanent gases, CO, $CO_2$, $H_2O$). The unit is controlled via a central system for recording the measurement values.

For the reactions under pressure, an analogous fixed bed tube reactor of V4A with a downstream pressure retention valve is employed.

All the catalysts are analysed by TEM (transmission electron microscopy) in respect of the size of the gold particles.

In example 20, ethylene is employed instead of propene.

In example 21, 1-butene is employed instead of propene.

Example 1

100 mg $H(AuCl_4)\times H_2O$, dissolved in 100 ml deionized water, are added dropwise to a suspension of 10 g titanium oxide hydrate (BET surface area of 380 m$^2$/g, 12% water) in 0.3 l deionized water at RT in the course of 60 min, while stirring. To precipitate the gold hydroxide, the pH is brought to 8 with a 0.5 molar $Na_2CO_3$ solution; the pale yellow suspension loses its colour. The suspension is stirred at RT for 3 h, and the solid is separated off and washed 4 times with 25 ml completely demineralized water each time. For drying, the solid is kept at 150° C. for 2 h and at 200° C. for 1 h, and the dried contact is then calcined in air at 250° C. for 2 h and at 400° C. for 5 h.

A catalyst with 0.5 wt. % gold is obtained. Characterization by TEM shows nanoscale gold particles with average particle diameters of approx. 1–6 nm.

The results of the catalytic reaction, analogously to the standard reaction conditions, are summarized in table 1.

Example 2

The catalyst is prepared analogously to example 1, but the aqueous suspension is heated up to 80° C. before the addition of the gold.

A catalyst with 0.5 wt. % gold is obtained. Characterization by TEM shows nanoscale gold particles with average particle diameters of approx. 3–8 nm.

The results of the catalytic reaction, analogously to the standard reaction conditions, are summarized in table 1.

Example 3

The catalyst is prepared analogously to example 1, but 200 mg $H(AuCl_4)$, dissolved in 100 ml completely demineralized water, are added. A catalyst with 1.0 wt. % gold is obtained. Characterization by TEM shows nanoscale gold particles with average particle diameters of approx. 3–6 nm.

The results of the catalytic reaction, analogously to the standard reaction conditions, are summarized in table 1.

Example 4

The catalyst is prepared analogously to example 1, but 464 mg monosodium citrate are added 0.5 h after the gold hydroxide precipitation.

A catalyst with 0.5 wt. % gold is obtained. Characterization by TEM shows nanoscale gold particles with average particle diameters of approx. 1–6 nm.

The results of the catalytic reaction, analogously to the standard reaction conditions, are summarized in table 1.

Example 5

The catalyst is prepared analogously to example 1, but 464 mg magnesium citrate are added 0.5 h after the gold hydroxide precipitation.

A catalyst with 0.5 wt. % gold is obtained. Characterization by TEM shows nanoscale gold particles with average particle diameters of approx. 1–6 nm.

The results of the catalytic reaction, analogously to the standard reaction conditions, are summarized in table 1.

Example 6

The catalyst is prepared analogously to example 1, but the dried contact is calcined for only 1 h at 250° C. 10 g of this dried catalyst are again reacted with 100 mg $H(AuCl_4)$, washed, dried and calcined, analogously to example 1.

A catalyst with 1.0 wt. % gold is obtained. Characterization by TEM shows nanoscale gold particles with average particle diameters of approx. 1–6 nm.

The results of the catalytic reaction, analogously to the standard reaction conditions, are summarized in table 1.

Example 7

The catalyst is prepared analogously to example 1, but the titanium oxide hydrate contains 0.1% sulfate and 12% water.

A catalyst with 0.5 wt. % gold is obtained. Characterization by TEM shows nanoscale gold particles with average particle diameters of approx. 3–8 nm.

The results of the catalytic reaction, analogously to the standard reaction conditions, are summarized in table 1.

Example 8

The catalyst is prepared analogously to example 1, but the titanium oxide hydrate contains 4% sulfate and 12% water.

A catalyst with 0.5 wt. % gold is obtained. Characterization by TEM shows nanoscale gold particles with average particle diameters of approx. 3–8 nm.

The results of the catalytic reaction, analogously to the standard reaction conditions, are summarized in table 1.

Example 9

The catalyst is prepared analogously to example 1, but the calcining is carried out at 500° C. for 5 h.

A catalyst with 0.5 wt. % gold is obtained. Characterization by TEM shows nanoscale gold particles with average particle diameters of approx. 3–8 nm.

The results of the catalytic reaction, analogously to the standard reaction conditions, are summarized in table 1.

Example 10

The catalyst is prepared analogously to example 1, but a pH of 7.0 is established.

A catalyst with 0.5 wt. % gold is obtained. Characterization by TEM shows nanoscale gold particles with average particle diameters of approx. 3–8 nm.

The results of the catalytic reaction, analogously to the standard reaction conditions, are summarized in table 1.

Example 11

The catalyst is prepared analogously to example 1, but a pH of 7.5 is established.

A catalyst with 0.5 wt. % gold is obtained. Characterization by TEM shows nanoscale gold particles with average particle diameters of approx. 3–8 nm.

The results of the catalytic reaction, analogously to the standard reaction conditions, are summarized in table 1.

Example 12

The catalyst is prepared analogously to example 1, but ZnO is employed instead of titanium oxide hydrate.

A gold/zinc oxide catalyst with 0.5 wt. % gold is obtained. Characterization by TEM shows nanoscale gold particles with average particle diameters of approx. 3–10 nm.

The results of the catalytic reaction, analogously to the standard reaction conditions, are summarized in table 1.

Example 13

The catalyst is prepared analogously to example 1, but ZnO/3% $TiO_2$ (anatase) is employed instead of titanium oxide hydrate.

A gold/zinc oxide/titanium dioxide catalyst with 0.5 wt. % gold is obtained. Characterization by TEM shows nanoscale gold particles with average particle diameters of approx. 3–10 nm.

The results of the catalytic reaction, analogously to the standard reaction conditions, are summarized in table 1.

Example 14

100 mg $H(AuCl_4)$ are dissolved in 50 ml completely demineralized water, 10 g titanium oxide hydrate are introduced, while stirring, and the suspension is brought to pH 8 with 0.5 molar $Na_2CO_3$ solution. 464 mg magnesium citrate are then added. After stirring for 2 h, the solid is separated off, washed 5 times with 100 ml water, dried at 150° C. for 2 h and calcined at 400° C. for 5 h.

Characterization by TEM shows nanoscale gold particles with average particle diameters of approx. 1–6 nm.

The results of the catalytic reaction, analogously to the standard reaction conditions, are summarized in table 1.

Example 15

The catalyst is prepared analogously to example 14, but the oxidation reaction is carried out at 40° C.

Example 16

The catalyst is prepared analogously to example 14, but the oxidation reaction is carried out at 30° C.

Example 17

The catalyst is prepared analogously to example 16, but the dried contact is calcined for only 1 h at 250° C. 10 g of this dried catalyst are again reacted with 100 mg $H(AuCl_4)$, washed, dried and calcined, analogously to example 16.

A catalyst with 1.0 wt. % gold is obtained. Characterization by TEM shows nanoscale gold particles with average particle diameters of approx. 1–6 nm.

The results of the catalytic reaction, analogously to the standard reaction conditions, are summarized in table 1.

Example 18

The catalyst is prepared analogously to example 1, but the reaction analogously to the standard reaction conditions is carried out under an increased pressure of 3 bar.

The results of the catalytic reaction, analogously to the standard reaction conditions, are summarized in table 1.

Example 19

The catalyst is prepared analogously to example 1, but the reaction analogously to the standard reaction conditions is carried out under an increased pressure of 10 bar.

The results of the catalytic reaction, analogously to the standard reaction conditions, are summarized in table 1.

Example 20

The catalyst is prepared analogously to example 14, but ethylene is employed under the standard reaction conditions instead of propene.

The results of the catalytic reaction, analogously to the standard reaction conditions, are summarized in table 1.

Example 21

The catalyst is prepared analogously to example 14, but 1-butene is employed under the standard reaction conditions.

Comparison experiment 1:

A solution of 0.104 g $HAuCl_4 \times 4H_2O$ in 400 ml distilled water is heated up to 70° C. and brought to pH 7.5 with an aqueous 0.1 N NaOH solution, 5 g titanium dioxide (anatase/rutile mixed oxide; P 25 from Degussa) are added in one portion, with intensive stirring, and stirring is continued for 1 h. The solid is washed 5 times with 3 litres distilled water each time, dried at room temperature in vacuo for 12 hours and calcined at 400° C. for 4 h. A gold/titanium dioxide catalyst with 1 wt. % gold is obtained.

The results of the catalytic reaction, analogously to the standard reaction conditions, are summarized in table 1.

Comparison experiment 2:

300 ml of an aqueous solution, comprising 50 g (0.05 moles) of an aqueous 24 wt. % solution of $Ti(SO_4)_2$ (calculated as titanyl sulfate: $Ti(SO_4)_2 + H_2O = TiOSO_4 + H_2SO_4$) and 1.08 g $HAuCl_4$ dissolved therein, were added dropwise to 200 ml of an aqueous solution, comprising 22.3 g (0.21 moles) sodium carbonate dissolved therein, over a period of 30 min. 5 minutes after the end of the dropwise addition, the resulting aqueous suspension of the mixed precipitate and 400 ml of a saturated aqueous solution of magnesium citrate (6 g/l) were stirred continuously for 1 h for ageing. The pH was 8.3. After the precipitate had been washed, the solid was dried in vacuo and calcined at 400° C. for 5 h.

A gold/titanium dioxide catalyst with 11 wt. % gold was obtained.

The results of the catalytic reaction, analogously to the standard reaction conditions, are summarized in table 1.

TABLE 1

| Catalyst | Propene oxide selectivity (%) | Propene oxide yield (%) |
|---|---|---|
| Example 1 | >97 | 5.1 |
| Example 2 | >97 | 4.7 |
| Example 3 | >97 | 3.4 |
| Example 4 | >97 | 5.6 |
| Example 5 | >97 | 5.6 |
| Example 6 | >97 | 5.8 |
| Example 7 | >97 | 4.0 |
| Example 8 | >97 | 3.7 |
| Example 9 | >97 | 5.4 |
| Example 10 | >97 | 3.5 |
| Example 11 | >97 | 4.4 |
| Example 12 | >97 | 0.4 |
| Example 13 | >97 | 0.9 |
| Example 14 | >97 | 5.7 |
| Example 15 | >97 | 5.1 |
| Example 16 | >97 | 4.6 |
| Example 17 | >97 | 5.7 |
| Example 18 | >97 | 5.7 |
| Example 19 | >97 | 4.9 |
| Example 20 | >97 | 5.0 |
| Example 21 | >97 | 5.5 |
| Comparison example 1 | >97 | 1.4 |
| Comparison example 2 | >97 | 0.5 |

What is claimed is:

1. A supported catalyst coated with gold particles comprising titanium oxide hydrate coated with from 0.05 to 10% by weight, based on the weight of the support, of nanoscale gold particles which has been calcined.

2. A process for the production of the catalyst of claim 1 comprising
   a) coating titanium oxide hydrate with from 0.05 to 10% by weight, based on the weight of the support, nanoscale gold particles by the deposition-precipitation method,
   b) washing the product of a),
   c) drying the product of b), and
   d) calcining the product of c).

3. The process of claim 2 in which step a) is repeated before step b) is carried out.

* * * * *